US005241958A

United States Patent [19]

Noeldner

[11] Patent Number: 5,241,958

[45] Date of Patent: Sep. 7, 1993

[54] THERAPEUTIC WHIRLPOOL UNIT WITH TEMPERATURE CONTRAST

[76] Inventor: David R. Noeldner, 1210 Mayfair Dr., Watertown, S. Dak. 57201

[21] Appl. No.: 743,184

[22] Filed: Aug. 9, 1991

[51] Int. Cl.[5] .............................................. A61F 33/02

[52] U.S. Cl. ....................................... 607/86; 4/541.4; 607/87; 607/104; 607/108

[58] Field of Search ................. 128/369, 370, 66, 375; 4/542, 543, 541

[56] References Cited

U.S. PATENT DOCUMENTS

| | | | |
|---|---|---|---|
| 1,963,557 | 6/1934 | Pain | 128/370 |
| 1,970,013 | 8/1934 | Mahmourian | 128/370 |
| 2,272,481 | 2/1942 | Rinkes et al. | 128/66 |
| 3,272,201 | 9/1966 | Barns | 128/66 |
| 3,477,424 | 11/1969 | Tracy | 128/375 |
| 4,217,892 | 8/1980 | Brill | 128/66 |
| 4,281,423 | 8/1981 | Fukanaga | 128/66 |
| 4,742,456 | 5/1988 | Kamena | 4/542 |
| 4,761,838 | 8/1988 | Hargrove | 128/66 |

FOREIGN PATENT DOCUMENTS 2645888 4/1978 Fed. Rep. of Germany ........ 128/66

*Primary Examiner*—Mark S. Graham
*Attorney, Agent, or Firm*—Jacobson, Price, Holman & Stern

[57] ABSTRACT

A whirlpool bath unit and more particularly a therapeutic whirlpool unit providing a container to receive a quantity of water and a portion of the human anatomy immersed in the water combined with air circulating bottom member in the container to provide a whirlpool bath and sequentially introducing and removing water having contrasting temperature levels in relation to the container while monitoring and controlling the temperature level and duration that water of a particular temperature occupies the container. The container is communicated with a pair of water reservoirs through a pump system with the water in each of the reservoirs being maintained at contrasting temperatures with the pump system removing water from the container into one of the reservoirs and introducing water into the container from the other reservoir which contains water of a contrasting temperature.

13 Claims, 2 Drawing Sheets

THERAPEUTIC WHIRLPOOL UNIT WITH TEMPERATURE CONTRAST

BACKGROUND OF INVENTION

1. Field of the Invention

The present invention generally relates to a whirlpool bath unit and more particularly a therapeutic whirlpool unit providing a container to receive a quantity of water and a portion of the human anatomy immersed in the water combined with air circulating means to provide a whirlpool bath and sequentially introducing and removing water having contrasting temperature levels in relation to the container while monitoring and controlling the temperature level and duration that water of a particular temperature occupies the container. The container is communicated with a pair of water reservoirs through a pump system with the water in each of the reservoirs being maintained at contrasting temperatures with the pump system removing water from the container into one of the reservoirs and introducing water into the container from the other reservoir which contains water of a contrasting temperature.

2. Description of the Prior Art

Various types of whirlpool baths are well known in which pressurized air is used to circulate water in a container in which a portion of the human anatomy is immersed for therapeutic purposes. The following U.S. patents disclose known structures providing this function. U.S. Pat. Nos. 3,373,740, 3,458,874, 3,772,714, 4,099,522, 4,385,724.

The prior art does not disclose a tank or container associated with two reservoirs containing water of contrasting temperatures together with heating systems, pumping systems and control systems as well as air circulating systems to sequentially subject the portion of the human anatomy to water of contrasting temperatures while circulating the water as disclosed in this invention.

SUMMARY OF THE INVENTION

An object of the present invention is to provide a therapeutic whirlpool unit capable of subjecting a portion of the human anatomy to circulating water in which the water in contact with the portion of the human anatomy is sequentially replaced by water at a contrasting temperature.

Another object of the invention is to provide a therapeutic whirlpool unit with temperature contrast which includes an open topped container with an optional top receiving a quantity of water at contrasting temperatures with pump units interconnecting the reservoirs and container or tank to pump water from one reservoir at a predetermined temperature into the tank for a predetermined time period and then remove that water and pump it back into the reservoir and then pump water from the other reservoir at a contrasting temperature into the container for a predetermined duration with the sequence being repeated during a treatment cycle.

A further object of the invention is to provide a therapeutic whirlpool unit in accordance with the preceding objects in which the container or tank is open topped and provided with an inclined perforated bottom associated with an air circulating device to cause aeration and circulation of the water in relation to a portion of the human anatomy placed on the inclined bottom surface of the container or tank.

Still another object of the present invention is to provide a therapeutic unit utilizing water circulated by air discharged through perforations in a hollow bottom structure to provide a therapeutic modality utilizing contrasting water baths and whirlpools massage which is relatively simple in construction and inexpensive to manufacture, operate and maintain.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
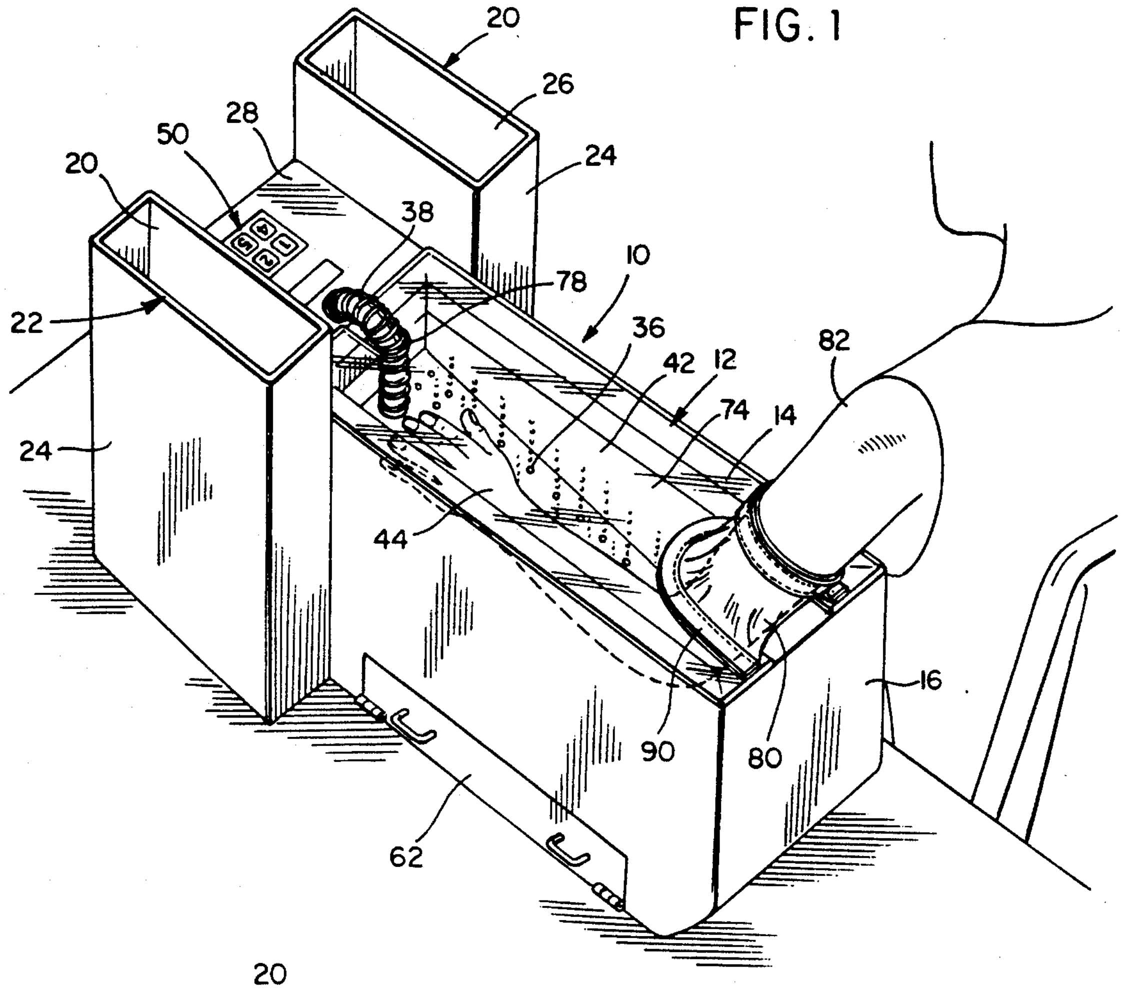
FIG. 1 is a perspective view illustrating the association of components of the present invention.

Referring now specifically to the drawings, the therapeutic whirlpool unit is generally designated by reference numeral 10 and includes a centrally located, generally rectangular compartment 12 forming an open topped container or tank 14 including vertically disposed imperforate end walls 16 and side walls 18 which may be constructed of metal, ceramic material, plastic material or the like providing an internal surface which is easy to clean and the walls may be appropriately insulated. Positioned alongside of and connected with the compartment 12 is a pair of water reservoirs 20 and 22 with each reservoir including vertical walls 24 forming an open topped reservoir 26. Intermediate the reservoirs 20 and 22, a housing 28 is provided which interconnects the reservoirs 20 and 22 and also connects with one end of the central compartment 12. The reservoir 20 is a cool water reservoir and the reservoir 22 is a warm water reservoir with the open top enabling a predetermined quantity of water to be placed in each reservoir. A removable cap or top may be provided for each of the reservoirs if desired.

The bottom of the container or tank 14 is a hollow bottom generally designated by reference numeral 30 including a top wall 32 and an imperforate bottom wall 34 spaced therefrom to provide a hollow bottom in which the top wall 32 is provided with a plurality of apertures or perforations 36 by which air can pass upwardly through the top plate 32. An air hose 38 connected with an air pump or blower 40 positioned within the housing 28 is connected to and provides pressurized air into the hollow bottom 30 in order for the pressurized air to pass upwardly through the apertures 36 for circulating and agitating a quantity of water 42 in the container or tank 14 to subject a portion of the human anatomy such as the hand and forearm 44 to the therapeutic benefits of a whirlpool bath with the arm and hand being positioned at an inclined angle corresponding to the inclined angle of the hollow bottom 30.

Positioned within the housing 28 is a pumping system for transferring water between the reservoirs 20 and 22 and the container or tank 14. The pumping system includes four pumps 46 with each reservoir having two pumps associated therewith with one of the pumps pumping water from the reservoir into the container or tank and the other pump pumping water out of the container or tank back into the reservoir. The pumps are non-submersible conventional structures powered individually by a conventional electric motor located within each pump. The warm water reservoir 22 optionally includes a heating unit 48 provided with a thermostatic control to maintain the temperature of the water in the reservoir 22 at a predetermined warm temperature higher than the temperature in the cool water reservoir 20 which will remain at room temperature or, if desired, a small self-contained refrigeration unit to maintain a desired cooler temperature.

Positioned in the housing 28 is a control apparatus generally designated by reference numeral 50 which controls operation of the therapeutic whirlpool unit which may include a computer which will monitor and control the water temperature in each reservoir and control operation of the pumps in a manner to introduce water at one temperature into the container or tank 14 from one of the reservoirs and operate the air pump or blower thus subjecting the hand and arm 44 to a whirlpool bath at a predetermined temperature and a predetermined duration. After the therapeutic treatment at this temperature, the water in the container or tank 14 is pumped back into the reservoir from which it was pumped thus emptying the container or tank. As soon as this operation is completed, another pump unit pumps water at a contrasting temperature from the other reservoir into the container or tank 14 thus subjecting the arm and hand 44 to a therapeutic whirlpool bath of a contrasting temperature for a predetermined time period after which another pump pumps that water back into the reservoir from which it was taken with the treatment cycle being repeated to subject the portion of the human anatomy positioned in the container or tank to whirlpool baths of contrasting temperatures and predetermined duration periods.

The therapeutic whirlpool unit 10 is particularly adapted for subjecting the hand and arm to contrasting temperature whirlpool baths which enables occupational and physical therapists to treat various conditions such as arthritis, hand injuries, reflex sympathetic dystrophy, burns, stroke and other conditions relating to the hands and forearms. Other extremities of the human anatomy could also be treated using the same techniques with possible variations in size characteristics. The therapeutic unit 10 provides a compact and cost effective unit which incorporates the technique of contrasting temperature whirlpool baths which can be used in the home or in a therapy clinic and is effective as a means for reducing edema, reducing pain as well as increase the range of motion of a joint such a those at the elbow, wrist and fingers. In addition, the device is effective for cleansing of wounds and desensitization of the upper extremities of the human anatomy. The water capacity of the container or tank 14 may vary but is preferably approximately six gallons with the reservoirs being capable of storing at least the same amount of water. Thus, the device may have an overall height of 12", a length of 40" and width of 15" although these dimensions may vary. The generally rectangular structure may be constructed of a foam plastic such as polystyrene foam available under the trademark "Styrofoam" forming the walls of the container or tank and reservoirs with the thickness of the walls being 1.5" to provide adequate strength and insulating properties with the interior surfaces or all surfaces of the tank and reservoirs being provided with a gel coat to provide a smooth, easily cleanable surface. A hard plastic could also be used and insulated for additional sturdiness.

A whirlpool bath effect is achieved by the use of the air pump or blower powered by a small motor which blows air through the hose into the hollow bottom unit for discharge through the air outlet holes 36. The control unit or computer 50 monitors the temperature in the reservoirs as indicated by thermostats and enables adjustments of and provides a display of the water temperature in both of the reservoirs as well as in the container or tank. In most treatment modalities, the reservoirs may simply be tank-like containers having an inclined bottom with a drain at the lower end which enables one reservoir to be filled with warm water and the other reservoir filled with cold water at predetermined temperatures with both reservoirs being monitored for the appropriate temperature. Warm water is then initially pumped into the tank 14 and the air pump or blower operates for about 4 minutes to provide a warm whirlpool bath. The tank would then be emptied by pumping the warm water back into the reservoir 22 and cold water is then introduced into the tank by pumping cold water from the reservoir 20 into the tank. While the cold water is in the tank, the warm water is being monitored at a predetermined temperature in the reservoir 22 and if necessary, a heater can be provided and actuated or if the warm water maintains a predetermined temperature, a heater may or may not be necessary. The cold water provides a cold whirlpool bath as the air pump or blower is continually operating and the cold whirlpool bath would last for a predetermined time period such as one minute before the cold water is drained and pumped back to the cold water reservoir 20 with warm water then being again pumped into the tank.

As a general rule, the contrast bath is a sequence of three temperature changes, beginning with warm water, then cool water and ending with warm water with the total treatment time including filling of the reservoirs with warm and cold water, going through the treatment cycle and then draining all water from the therapeutic unit through drains 52 not exceeding about twenty minutes.

Three drains 52 are provided in the front of the unit for easy access with each drain including a discharge nozzle, manual valve and a clear plastic hose 54 extending between the drain and the storage compartments and central compartment respectively along the floor of the computer/blower floor. Each hose may have a screen in the inlet end and may be removable to facilitate cleaning. The central compartment is provided with a floor 56 which is inclined downwardly at a small angle toward the front of the unit to promote water drainage in relation to the pumps and the clear plastic hose leading to the drains 52. Each of the storage compartments or reservoirs 20 and 22 is provided with an inclined bottom 58 at a slight angle to promote water drainage.

Below the floor 56 of the central compartment 12, a storage area 60 is provided which houses the pumps 46 and is isolated from the compartment or tank 12. Access can be had to the storage area from both sides by a closure door 62 which can be opened to enable articles to be stored in the area or removed therefrom. The storage area 62 includes a bottom wall 64 forming a closure for the bottom of the unit.

The pump units 46 are positioned in one end of the storage area 60 with 2 pumps adjacent each side of the storage area 60 in their own compartment 66. The pumps adjacent the storage area 60 drain the water from the central compartment 12 and pump it into the reservoirs and the pumps remote from the storage area 60 fill the central compartment with the pumps providing complete drainage and refilling the central compartment 12 and the reservoirs 20 and 22. The portion of the bottom wall 64 which closes the pump compartment 66 is removable to provide access to the pumps in the event maintenance becomes necessary. Likewise, the bottom of the compartment 68 for the blower unit 40 and control computer 50 has a removable cover to provide access if maintenance is required.

Figure 2:
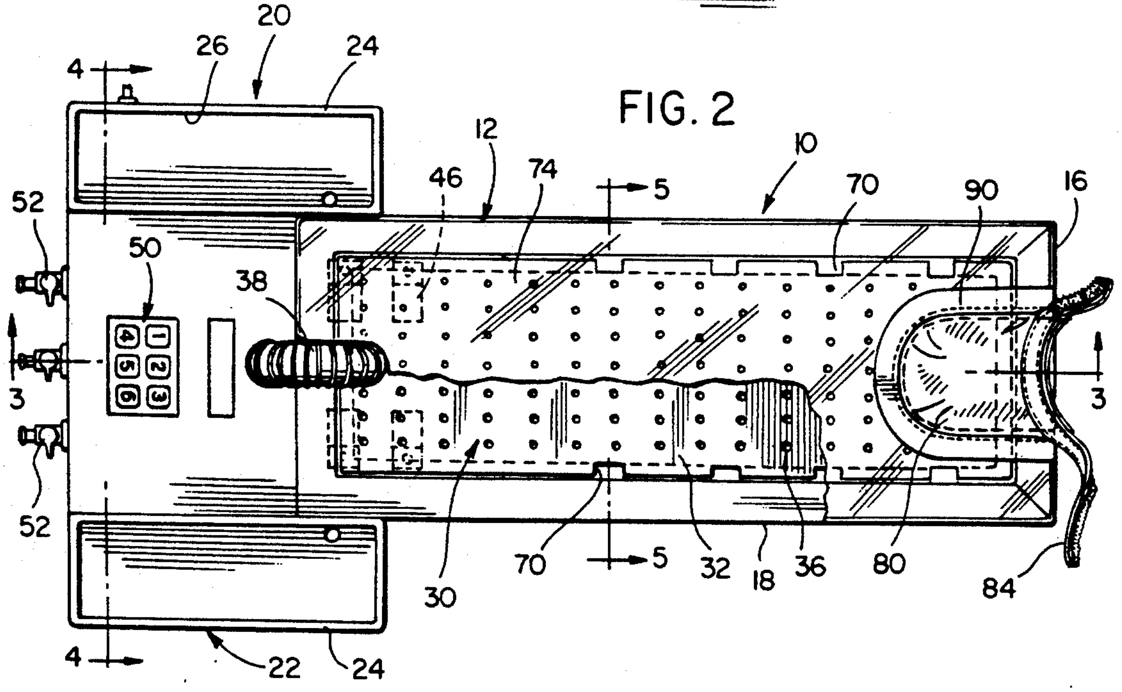
FIG. 2 is a top plan view of the device illustrating the association of the container or tank and water reservoirs.
Figures 3, 4, 5:
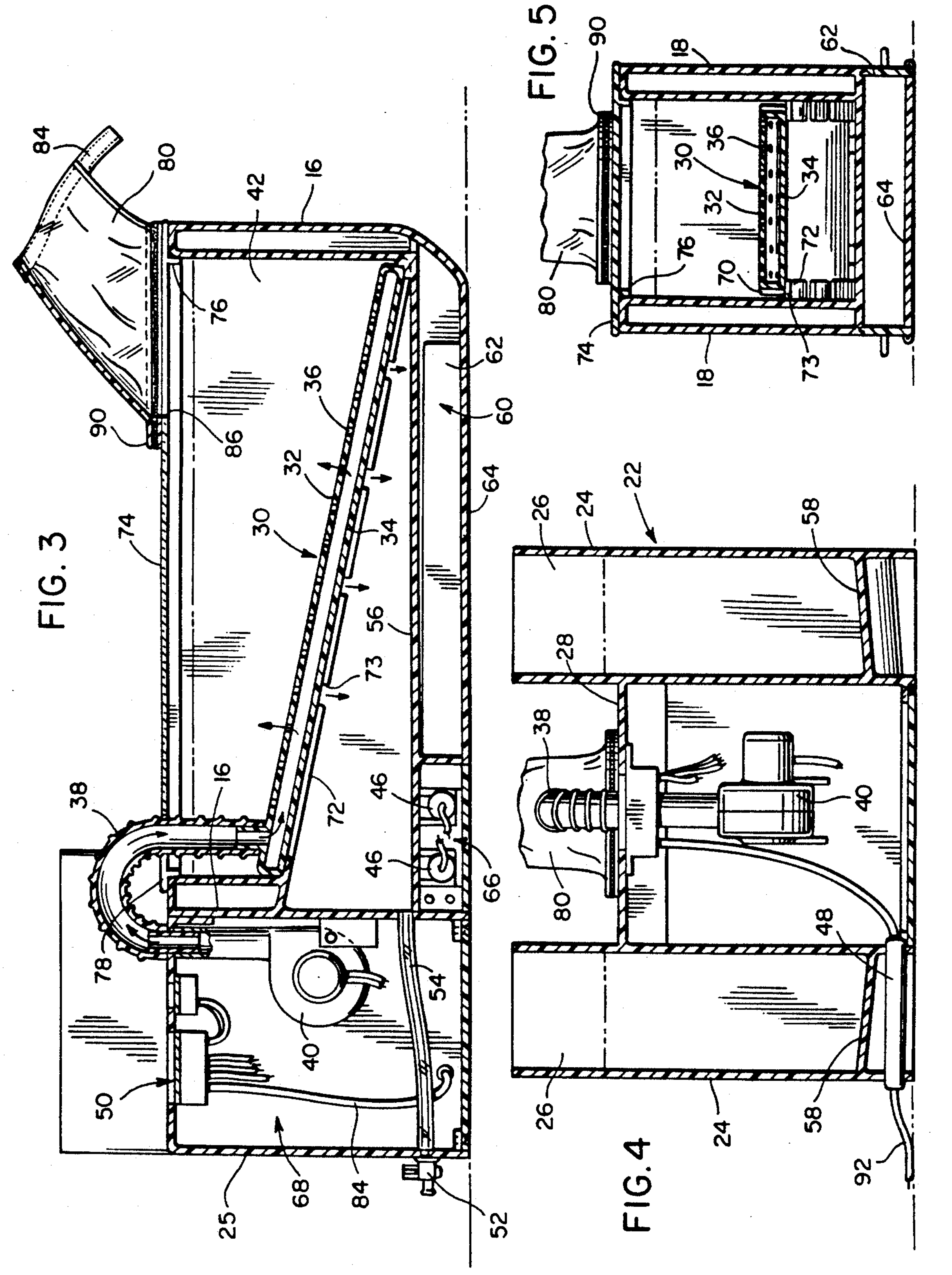
FIG. 3 is a longitudinal sectional view taken along section line 3—3 on FIG. 2 illustrating further structural details of the invention.
FIG. 4 is a transverse sectional view taken along section line 4—4 on FIG. 2 illustrating further structural details of the invention.
FIG. 5 is a transverse sectional view taken along section line 5—5 on FIG. 2 showing details of the tank.

As illustrated in FIG. 2, the aeration floor or hollow bottom 30 has a plurality of passageways 70 around the periphery thereof which enables water to pass therethrough when the water pumps are filling or draining the central compartment 12 which has notches 73 aligned with the passageways 70. The aeration floor 30 is removably supported in the central compartment 12 by a peripheral inwardly extending rib or flange 72 on the interior wall of the central compartment 12. This enables the aeration floor 30 to be removed by disconnecting the air hose 38 for cleaning the aeration floor and the interior of the central compartment.

Also, as illustrated, the open top of the central compartment can be closed by a transparent cover 74 to prevent spillage of water during use. The cover 74 sits on a depending lip 76 which telescopes into the upper end of the peripheral wall 16 and includes a notch 78 in one end receiving air hose 38 and a waterproof fabric member 80 at the other in the form of an openable sleeve secured around the upper arm 82 by a strap 84 provided with hook and loop fasteners such as "Velcro". The flexible fabric member 80 is removably attached peripherally of an opening 86 in the cover 74 for cleaning by a "Velcro" fastener base flange 90.

During the treatment cycle, a therapist can be engaged in other activities such as providing similar treatment cycles to other clients thus enabling the therapist to more effectively treat multiple clients in an effective manner. The open top of the tank and removable cover enables the therapist to manipulate the extremity if desired. If desired, the unit can be permanently installed with plumbing connections for filling the reservoirs and draining water from the unit or it may be constructed as a mobile unit independent of plumbing connections. A suitable electric power cord 92 provided with a conventional male plug may be used to supply electrical energy to the system in a conventional and well known manner.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A therapeutic whirlpool bath unit comprising an open topped container adapted to receive a quantity of water in which a portion of the human anatomy can be immersed, a pair of independent water reservoirs adjacent said container with one reservoir adapted to receive a quantity of warm water and the other reservoir adapted to receive a quantity of water at a lower temperature, pump means for sequentially introducing water from one reservoir into the container for a predetermined time period and then removing the water from the container and pumping it back into the one reservoir and then pumping water from the other reservoir into the container for a predetermined time and pumping the water back into the other reservoir to cyclicly provide a water bath of contrasting temperatures to the portion of the human anatomy in the container and means introducing pressurized air into the water in the container for circulating the water in relation to the portion of the human anatomy positioned in the container, a removable cover mounted in closing relation to the top of the open-topped container, said cover including a depending peripheral flange telescopically engaging top of the container, an arm receiving opening in said cover, a flexible sleeve attached to the opening, said sleeve including means retaining the sleeve in snug encircling relation to the arm to prevent water from splashing through the opening in the cover, said cover including an air supply hose opening therethrough in spaced relation to said arm receiving opening, said means for circulating the water in relation to the portion of the human anatomy including an aeration floor in the container, and an air hose connected to said aeration floor and extending through the air supply hose opening in the cover for communication with a source of pressurized air.

2. The structure as defined in claim 1 wherein said aeration floor includes an inclined hollow bottom member in said container communicated with said air hose, said bottom member including a perforated upper plate discharging air through the perforations into the water and a bottom plate, means on said container supporting said inclined bottom member whereby said bottom member forms a support for supporting the portion of the human anatomy immersed in the container in an inclined position.

3. The structure as defined in claim 2 wherein said container and reservoirs are connected to each other and control means between the reservoirs to indicate the water temperature in the container and each of the reservoirs thereby monitoring the temperature conditions of the whirlpool unit.

4. The structure as defined in claim 3 wherein the container is generally an elongated rectangular tank adapted to receive the hand, forearm and elbow area of a person receiving a whirlpool bath treatment.

5. The structure as defined in claim 4 wherein said container and reservoirs include inclined bottoms to facilitate drainage of the water therefrom.

6. The structure as defined in claim 1 wherein said container includes an inclined rib on the interior thereof, said aeration floor being removably supported in inclined position on said rib.

7. The structure as defined in claim 6 wherein said container includes a storage compartment isolated from water in the container, said storage compartment being in the bottom of the container.

8. The structure as defined in claim 6 wherein said container and reservoirs are provided with drain means to drain water therefrom, said drain means being drain valves located adjacent each other at one end of the unit and communicated with the container and reservoirs, respectively.

9. The structure as defined in claim 6 wherein said pump means includes independent pumps for pumping water between the reservoirs and container.

10. The structure as defined in claim 6 wherein said aeration floor includes an inclined hollow bottom member in said container communicated with said air hose, said bottom member including a perforated upper plate discharging air through the perforations into the water and a bottom plate engaging said rib, said hollow bottom member forming a support for the portion of the human anatomy immersed in the container in an inclined position.

11. The structure as defined in claim 10 wherein said container and reservoirs are connected to each other and control means between the reservoirs to indicate the water temperature in the container and each of the reservoirs thereby monitoring the temperature conditions of the whirlpool unit.

12. The structure as defined in claim 11 wherein the container is a generally elongated rectangular tank adapted to receive the hand, forearm and elbow area of a person receiving a whirlpool bath treatment.

13. A therapeutic whirlpool bath unit comprising a rigid open topped container adapted to receive a quantity of water in which a portion of the anatomy can be immersed, a pair of independent water reservoirs adjacent said container with one reservoir receiving a quantity of warm water and the other reservoir receiving a quantity of water at a lower temperature, pump means for introducing warm water from said one reservoir into the container for immersing the portion of the anatomy in the warm water for a predetermined time period and then pumping all of the warm water back into said one reservoir and then pumping water at a lower temperature from said other reservoir into the container for immersing the portion of the anatomy in the lower temperature water for a predetermined time and pumping all of the water back into said other reservoir to cyclicly provide a static water bath of contrasting temperatures to the portion of the anatomy positioned in the container and means introducing pressurized air into only a bottom portion of said container for movement upwardly in the water in the container for discharge from the open top thereby circulating the water in relation to the portion of the anatomy positioned in the container, said means for circulating the water including an inclined hollow bottom member in said container communicated with a source of pressurized air, said bottom member including a generally flat perforated upper plate positioned below an upper level of the static water bath in said container and occupying substantially the entire area of said container, said upper plate having perforations throughout the area of the plate for discharging air through the perforations into the water throughout the area of the container, said inclined bottom member forming a support for supporting the portion of the anatomy immersed in the container in an inclined position.

* * * * *